(12) United States Patent
Yamashita et al.

(10) Patent No.: US 9,541,518 B2
(45) Date of Patent: Jan. 10, 2017

(54) ELECTROCHEMICAL DETECTOR AND METHOD FOR PRODUCING SAME

(71) Applicant: PANASONIC INTELLECTUAL PROPERTY MANAGEMENT CO., LTD., Osaka (JP)

(72) Inventors: Yoshihisa Yamashita, Kyoto (JP); Seiichi Nakatani, Osaka (JP); Tetsuyoshi Ogura, Osaka (JP); Koichi Hirano, Osaka (JP); Makoto Takahashi, Osaka (JP); Satoshi Arimoto, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 467 days.

(21) Appl. No.: 14/131,522

(22) PCT Filed: Dec. 12, 2012

(86) PCT No.: PCT/JP2012/007951
§ 371 (c)(1),
(2) Date: Jan. 8, 2014

(87) PCT Pub. No.: WO2013/171815
PCT Pub. Date: Nov. 21, 2013

(65) Prior Publication Data
US 2014/0151225 A1     Jun. 5, 2014

(30) Foreign Application Priority Data

May 17, 2012  (JP) ................................. 2012-113659

(51) Int. Cl.
*G01N 27/327*    (2006.01)
*G01N 27/30*     (2006.01)
*H01R 43/16*     (2006.01)

(52) U.S. Cl.
CPC .......... *G01N 27/30* (2013.01); *G01N 27/3277* (2013.01); *H01R 43/16* (2013.01); *Y10T 29/49204* (2015.01)

(58) Field of Classification Search
None
See application file for complete search history.

(56) References Cited

U.S. PATENT DOCUMENTS 5,627,022 A     5/1997   Renfrew et al.
5,885,431 A     3/1999   Renfrew et al.
(Continued)

FOREIGN PATENT DOCUMENTS

CN     1162995     10/1997
CN     1463361     12/2003
(Continued)

OTHER PUBLICATIONS

Chinese Office Action (OA) and Search Report (SR) issued Apr. 3, 2015 in corresponding Chinese Patent Application 201280034303.4, together with English translations thereof.
(Continued)

*Primary Examiner* — J. Christopher Ball
(74) *Attorney, Agent, or Firm* — Wenderoth, Lind & Ponack, L.L.C.

(57) ABSTRACT

An electrochemical detector is an electrochemical detector for detecting a substance in a liquid by generating a redox cycle, the electrochemical detector comprising: a first working electrode having a first electrode surface, a second working electrode having a second electrode surface, and a plurality of insulating spacer particles, wherein the first and second electrode surfaces are placed so as to face each other so that an electric field is formed between the first and second electrode surfaces, and the plurality of spacer particles are placed along the first and second electrode surfaces
(Continued)

so as to separate the first and second electrode surfaces from each other.

20 Claims, 8 Drawing Sheets

(56) References Cited

U.S. PATENT DOCUMENTS

| | | | |
|---|---|---|---|
| 2003/0150745 | A1* | 8/2003 | Teodorczyk ......... A61B 5/1411 205/775 |
| 2004/0005721 | A1 | 1/2004 | Tanike et al. |
| 2006/0175205 | A1 | 8/2006 | Cui et al. |
| 2009/0184004 | A1 | 7/2009 | Chatelier et al. |
| 2009/0211922 | A1 | 8/2009 | Sasaki et al. |
| 2013/0068633 | A1 | 3/2013 | Chatelier et al. |
| 2013/0098763 | A1 | 4/2013 | Chatelier et al. |

FOREIGN PATENT DOCUMENTS

| | | |
|---|---|---|
| EP | 0 569 908 | 11/1993 |
| JP | 1-272958 | 10/1989 |
| JP | 3-246460 | 11/1991 |
| JP | 6-27081 | 2/1994 |
| JP | 10-512043 | 11/1998 |
| JP | 2001-21528 | 1/2001 |
| JP | 2006-215034 | 8/2006 |
| JP | 2006-250560 | 9/2006 |
| JP | 2009-168815 | 7/2009 |
| WO | 02/097418 | 12/2002 |
| WO | 2009/057240 | 5/2009 |

OTHER PUBLICATIONS

Notification of Transmittal of Translation of the International Preliminary Report on Patentability (IPROP) issued Nov. 27, 2014 in International (PCT) Application No. PCT/JP2012/007951, together with IPROP and translation of Written Opinion.

Chinese Office Action issued Sep. 30, 2014 in corresponding Chinese Patent Application No. 201280034303.4, together with English translation thereof.

Chinese Search Report issued Sep. 30, 2014 in corresponding Chinese Patent Application No. 201280034303.4, together with English translation thereof.

International Search Report (ISR) issued Jan. 15, 2013 in International (PCT) Application No. PCT/JP2012/007951.

* cited by examiner

ELECTROCHEMICAL DETECTOR AND METHOD FOR PRODUCING SAME

TECHNICAL FIELD

The present invention relates to an electrochemical detector used for detectors, such as an electrochemical sensor and chromatography, in which the detectors are used for qualitative and quantitative analyses of ions, harmful substances, and physiologically active substances in a liquid, and a method for producing the same. In particular, it relates to an electrochemical detector which can detect a target substance with a high sensitivity and with a small amount of a solution, and a method for producing the same.

BACKGROUND ART

Electrochemical measurements are used for qualitative analysis of ions, molecules contained in a solution and the like. Working electrodes are immersed in a sample solution containing a test substance, and when the test substance is electrochemically reacted on the working electrodes, a value of an electric current flowing through the working electrodes is measured, whereby the test substance in the sample solution is detected.

As the electrochemical detector used for electrochemical measurements, those in which two comb-shaped working electrodes are combined are widely used (for example, Patent Document 1).

FIGS. 11A, 11B show an example thereof. FIG. 11A is a plan view of an electrochemical detector in which two comb-shaped electrodes are combined, and FIG. 11B is a cross-sectional view of FIG. 11A taken along line A-A'. In the electrochemical detector shown in FIGS. 11A, 11B, comb-shaped working electrodes 802 and 803 are formed on an insulating substrate 801 so as to engage with each other. An electrochemical measurement is performed in the following manner. First, droplets of a sample solution 200 containing a test substance are dropped on the electrochemical detector. Then, when different potentials are applied respectively to the working electrodes 802 and 803, the test substance is oxidized on one electrode (for example, 802), and then reduced on the other adjacent electrode (for example, 803) to return to the original substance. As a result, so-called redox cycling in which oxidation and reduction are repeated between the two electrodes 802 and 803 occurs.

FIG. 12 schematically shows redox cycles generated in the electrochemical detector in which the two comb-shaped electrodes are combined. A reductant Red, which is the test substance in the sample solution, is oxidized in the working electrode 802 to become an oxidant Ox, which is then oxidized in the adjacent other working electrode 803 to return to the original reductant Red. One reductant repeats oxidation and reduction, whereby the apparent quantity of an electric current flowing through the working electrodes is increased following the oxidation-reduction reactions.

Therefore, if an electrochemical measurement is performed using such electrodes, the test substance in the sample solution can be detected with a high sensitivity. In particular, the higher the density between the adjacent two electrodes, where the oxidation-reduction reactions are generated, namely, in FIGS. 11A and 11B, as the width of the electrodes 802, 803 and a space between them become smaller, the number of occurrences of redox cycling per unit time is increased, so that a highly sensitive electrochemical measurement is enabled.

Recently, an electrochemical measurement using the electrochemical detector is also applied to a biosensor for measuring a protein such as an antigen in a living body. In this case, in order to detect the protein, for example, a complex between the protein and an enzyme-labeled antibody is formed. Further, the enzyme label of the complex is reacted with a substrate to produce a substance carrying out redox cycling (a redox species). Since the amount of the redox species produced is proportional to the amount of the protein, the produced redox species is detected by the electrochemical measurement, whereby the concentration of the protein can be indirectly measured.

CITATION LIST

Patent Document 1: Japanese Patent Application Laid-open Publication No. H01-272958

SUMMARY OF INVENTION

Technical Problem

However, the above conventional electrochemical detector in which the two comb-shaped working electrodes are combined has the following problems.

First, since the working electrodes 802, 803 are on the same plane, the sample solution is dropped on this plane, and held in a state in which it is swollen upward from this plane due to surface tension. When a voltage is applied, an electric field is generated between the working electrodes 802 and 803, but the intensity of the electric field becomes lower as it goes toward an upper portion of the sample solution. Therefore, for example, the test substance oxidized in the one electrode 802 is diffused to the upper portion of the sample solution without reaching the adjacent other working electrode 803, and is not reduced, so that a redox cycle is interrupted. As a result, an increase in electric current flowing through the working electrodes 802, 803 was suppressed, resulting in a deterioration of detection sensitivity.

On the other hand, the two comb-shaped working electrodes 802 and 803 are formed by microfabricating a thin film-shaped conductive material using a publicly known photolithography technology. As described above, for an improvement in detection sensitivity of the electrochemical measurement using them, it is required to reduce the electrode width of the working electrodes and the space between them. However, such microfabrication requires a very high processing technology and an expensive processing device, which has become a factor for an increase in cost.

The present invention was made in view of the above points. It is an object of the present invention to provide an electrochemical detector which enables an electrochemical measurement with a high sensitivity and which can be fabricated at a low cost, and a method for producing the same.

Solution to Problem

An electrochemical detector according to the present invention detects a substance in a liquid by generating a redox cycle, wherein the electrochemical detector comprises:
a first insulating substrate;
a first working electrode formed on one main surface of the first insulating substrate;
a second insulating substrate;

a second working electrode formed on one main surface of the second insulating substrate; and a plurality of insulating spacers, wherein the first and second electrodes are placed so as to overlap and face each other in plan view, and wherein the plurality of spacers are placed along the first and second electrodes so as to separate the first and second electrodes from each other.

A method for producing an electrochemical detector according to the present invention comprises:

a step of forming a first working electrode on one main surface of a first insulating substrate;

a step of forming a second working electrode on one main surface of a second insulating substrate;

a step of placing a plurality of spacers on the first working electrode; and a step of placing the second working electrode so that the first and second working electrodes overlap and face each other in plan view.

Advantageous Effects of Invention

In the electrochemical detector according to the present invention and the method for producing the electrochemical detector, it is possible to provide an electrochemical detector which enables a highly sensitive electrochemical measurement and which can be fabricated at a low cost, and a method for producing the same.

DESCRIPTION OF EMBODIMENTS

Figure 1A:
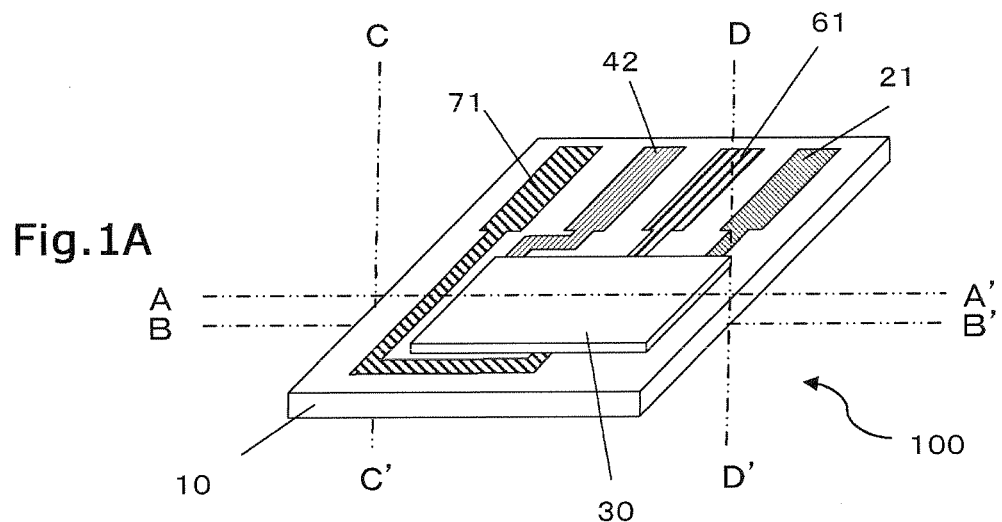
FIG. 1A is a perspective view schematically showing the structure of an electrochemical detector 100 of a first embodiment.

Embodiments according to the present invention will hereinafter be described with reference to the drawings. In the drawings below, for the sake of simplification of the description, components substantially having the same function are denoted by the same numerals. The present invention is not limited to the following Embodiments.

First Embodiment

With reference to FIGS. 1A, 1B, 2A and 2B, an electrochemical detector of a first embodiment will be described.

Figure 1B:
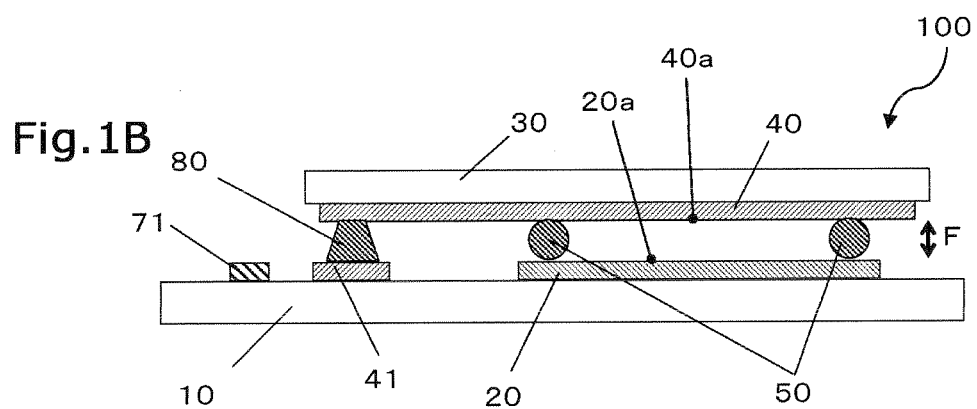
FIG. 1B is a view schematically showing the cross-sectional structure of FIG. 1A.

FIG. 1A is a perspective view schematically showing an electrochemical detector used in the first embodiment. FIG. 1B schematically shows the cross-sectional structure of the electrochemical detector which is cut out by a plane surrounded by lines A-A', B-B', C-C', and D-D' of FIG. 1A.

Figure 2A:
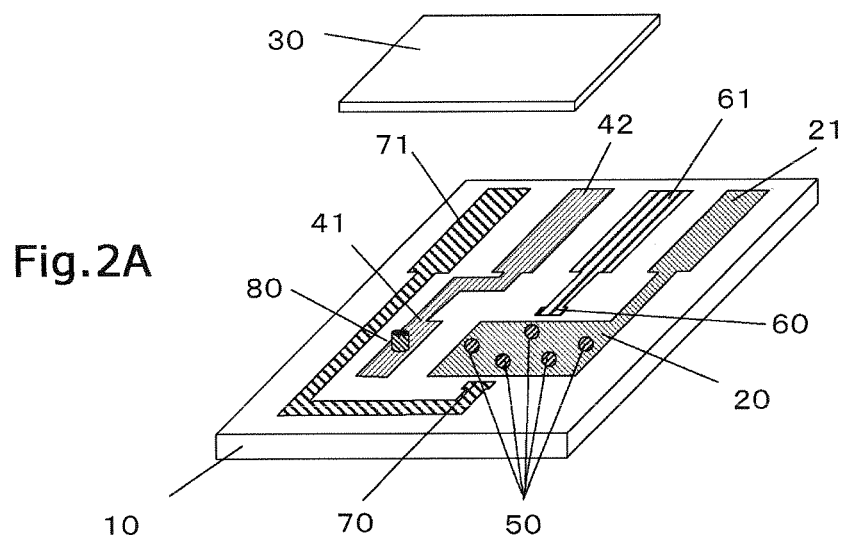
FIG. 2A is an exploded perspective view of the electrochemical detector 100 according to the first embodiment.
Figure 2B:
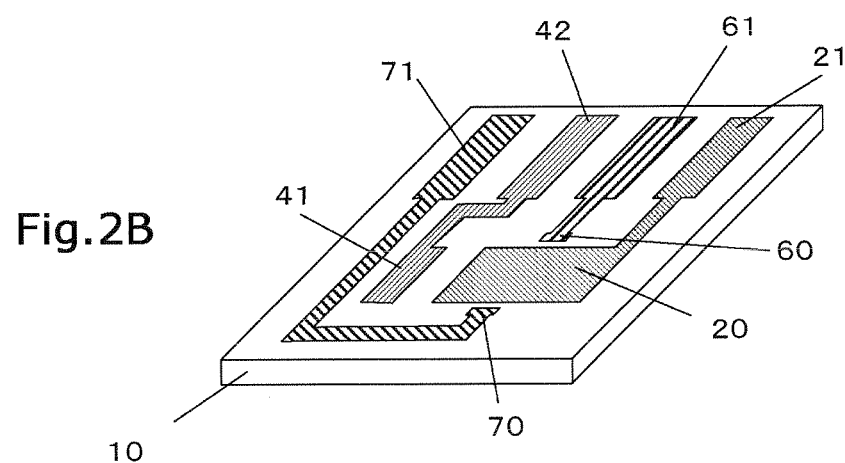
FIG. 2B is a perspective view of a first insulating substrate 10, as seen from one main surface thereof formed with a first working electrode 20, which constructs the electrochemical detector 100.
Figure 2C:
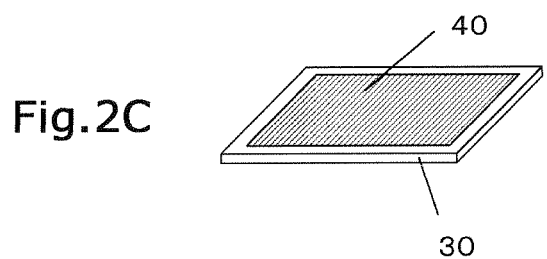
FIG. 2C is a perspective view of a second insulating substrate 30, as seen from one main surface thereof formed with a second working electrode 40.

FIG. 2A is an exploded perspective view of the electrochemical detector according to the first embodiment. FIG. 2B is a perspective view schematically showing a first insulating substrate 10, as seen from one main surface thereof formed with a first working electrode 20. FIG. 2C is a perspective view schematically showing a second insulating substrate 30, as seen from one main surface thereof formed with a second working electrode 40.

The electrochemical detector 100 has the first insulating substrate 10, the first working electrode 20 formed on the one main surface of the first insulating substrate 10, the second insulating substrate 30, the second working electrode 40 formed on the one main surface of the second insulating substrate 30, and a plurality of insulating spacer particles 50. The first working electrode 20 has a first electrode surface 20a, and the second working electrode 40 has a second electrode surface 40a. The first electrode surface 20a and the second electrode surface 40a are placed so as to face each other so that an electric field F is formed between the first electrode surface 20a and the second electrode surface 40a. In the first embodiment, the first electrode surface 20a and the second electrode surface 40a are planes and overlap in plan view. The plurality of spacer particles 50 are placed along the first electrode surface 20a and the second electrode surface 40a so as to separate the first electrode surface 20a and the second electrode surface 40a from each other.

Further, as the desired structure, the first insulating substrate 10 has a third electrode 41, and the third electrode 41 is electrically connected to the second working electrode 40 via a connection member 80.

Desirably, the first insulating substrate 10 further has a reference electrode 60 and a counter electrode 70 that are on the same surface as the first working electrode 20. Also, the first insulating substrate has lead-out electrodes 21, 42, 61, 71 for facilitating measurement. The first working electrode 20, the third electrode 41, the reference electrode 60, and the counter electrode 70 are electrically connected via wiring to the lead-out electrode 21, the lead-out electrode 42, the reference electrode 61 and the lead-out electrode 71, respectively.

The insulating substrates 10 and 30 may be formed of any material as long as the surface formed with the working electrode is insulating. For example, they are formed of a glass substrate, a resin substrate, a ceramic substrate, a quartz substrate or a silicon substrate with an oxide film. The insulating substrates 10 and 30 have a thickness of, for example, 100 µm to 2 mm.

The working electrodes 20 and 40 may be formed of a conductive material. For example, they are formed of a metal such as gold, platinum, silver, chromium, titanium or stainless, or a paste composition containing metal powder or conductive carbon powder. In particular, from the viewpoint of easiness in electron donation and acceptance for oxidizing or reducing a test substance, gold, platinum, or a paste composition containing conductive carbon powder is preferred. The working electrodes 20 and 40 have a thickness of, for example, 10 nm to 35 µm, a surface roughness of, for example, 0.01 µm to 1 µm in terms of center line average roughness Ra. The working electrodes 20 and 40 are not necessarily formed of one kind of conductive material. For example, they may be those electrodes having a laminated structure with two or more layers formed of different materials. In this case, surface layers of the working electrodes 20 and 40 are formed of a conductive material. These surface layers require conductivity because they are regions brought into contact with the test substance, namely, the substantial regions where electrons are donated to and accepted from the test substance to generate oxidation or reduction reaction. In this case, if the thickness of the conductive material of the surface layers is preferably 5 nm to 5 µm, for example, because if it is too small, a pin hole and the like occur.

The insulating spacer particles 50 may be formed of any material as long as they are particles whose surfaces are at least insulating, and they are formed of silica, glass, resin, or ceramic. The spacer particles 50 have a roll of a gap control in which the separation distance between the first working electrode 20 and the second working electrode 40 is kept constant. That is, the height of the spacer particles 50 in a direction perpendicular to the first working electrode 20 and the second working electrode 40 determines the separation distance between the first working electrode surface 20a and the second working electrode surface 40a. Their height is 20 nm or more and 3 µm or less, for example. Further, the number of spacer particles 50 is a number required to keep the separation distance between the working electrode 20 and the working electrode 40, which is at least 3 or more. If the number is too large, the spacer particles 50 cover surfaces of the working electrode 20 and the working electrode 40, so that an area of the working electrodes required for electrochemical reaction cannot be secured. Therefore, this number is practically 3 or more and 20 or less, for example. Further, the spacer particles 50 are placed on the first electrode surface 20a or the second electrode surface 40a. In the first embodiment, the second electrode surface 40a is larger than the first electrode surface 20a, and the entire first electrode surface 20a is located inside the second electrode surface 40a, and overlaps therewith in plan view. It is preferred that a surface density of the spacer particles 50 is 0.01/mm$^2$ or more and 1/mm$^2$ or less in this overlapped region. The spacer particles 50 have a spherical shape in FIG. 1B and FIG. 2A, but the shape is not limited to this. They may have an oval spherical shape or a cylindrical shape, for example, as long as the plurality of spacer particles 50 have a uniform height. It is preferred that the spacer particles 50 are fixed to at least one of the first working electrode 20 and the second working electrode 40 by bonding and the like.

The third electrode 41, the reference electrode 60, and the counter electrode 70 may be formed of a conductive material. For example, they are formed of a metal such as gold, platinum, silver, chromium, titanium or stainless, or a paste composition containing metal powder or conductive carbon powder. From the viewpoint of simplification of the production, the material, thickness, and surface roughness according to the third electrode 41 are the same as those of the first working electrode 20.

The connection member 80 may be formed of a conductive material. For example, it is formed of a metal such as gold, aluminum, copper or solder, or a paste composition containing metal powder or conductive carbon powder. The connection member 80 preferably has the same height as the spacer particles 50, which is 20 nm or more and 3 µm or less, for example. The number of connection members 80 is one in FIG. 2A, but it is not limitative. There may be the plurality of connection members 80.

Figure 3:
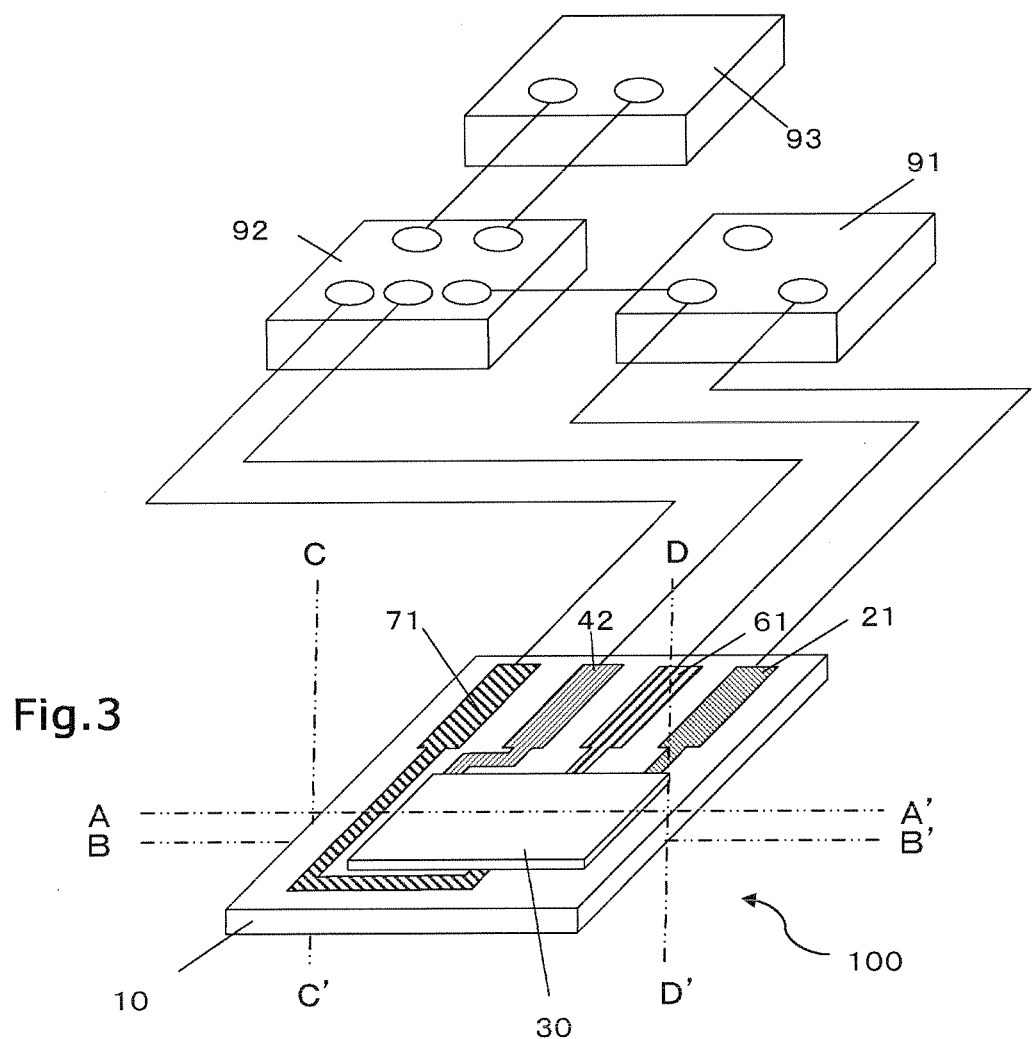
FIG. 3 is a perspective view schematically showing an electrochemical measurement device using the electrochemical detector 100 according to the first embodiment.

With reference to FIG. 3 and FIG. 4, a method for electrochemical measurement using the electrochemical detector 100 according to the first embodiment will be described.

FIG. 3 is a perspective view schematically showing an electrochemical measurement device using the electrochemical detector 100. The lead-out electrode 21 connected to the first working electrode 20 (FIG. 2A) is connected to a dual potentiostat 91. The lead-out electrode 42 connected to the second working electrode 40 (FIG. 2C) via the connection member 80 (FIG. 2A) and the third electrode 41 (FIG. 2B) is connected to a potentiostat 92. Also, the lead-out electrode 61 connected to the reference electrode 60 (FIG. 2A) is connected to the dual potentiostat 91 and the potentiostat 92. The lead-out electrode 71 connected to the counter electrode 70 (FIG. 2A) is connected to the potentiostat 92. Further, the potentiostat 92 is connected to a function generator 93.

In the electrochemical measurement device shown in FIG. 3, the potential of the first working electrode 20 is kept constant by the dual potentiostat 91, and the potential of the second working electrode 40 is changed by the function generator 93, whereby different potentials are given respectively to the first working electrode 20 and the second working electrode 40. The potential of the reference electrode 60 serves as a reference potential. In the electrochemical measurement, the sample solution containing the test substance is allowed to be present between the first working electrode 20 and the second working electrode 40, and different potentials are given respectively to the first working electrode 20 and the second working electrode 40. On the basis of the difference in potential, a redox cycle of the test substance is generated between the first working electrode 20 and the second working electrode 40 so that an electric current flows through the working electrodes 20, 40. By detecting this electric current value, the test substance can be detected.

Figure 4A:
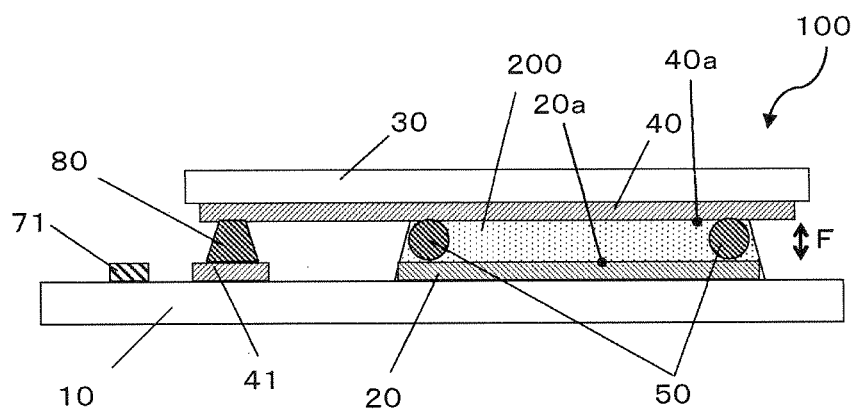
FIG. 4A is a view schematically showing the cross-sectional structure in which a sample solution 200 is brought into contact with the electrochemical detector 100 according to the first embodiment.
Figure 4B:
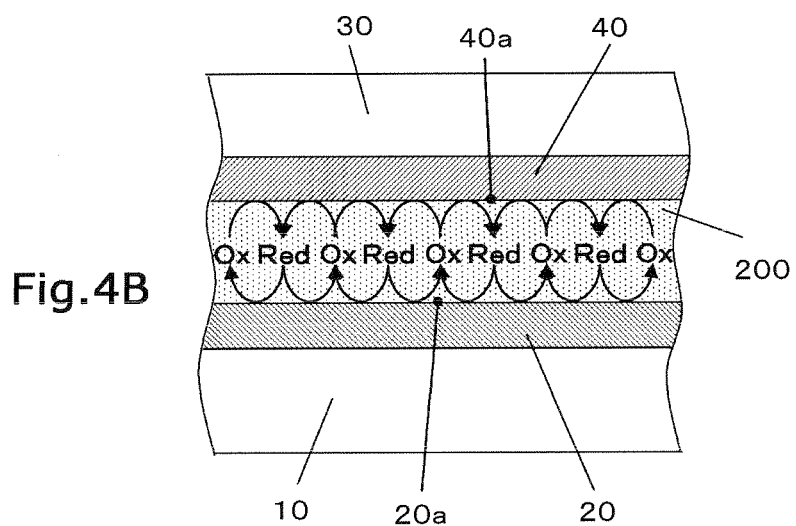
FIG. 4B is a cross-sectional view for explaining redox cycling that occurs in the electrochemical detector 100.

FIG. 4A schematically shows the cross-sectional structure when a sample solution 200 containing a test substance is allowed to be present between the first working electrode 20 and the second working electrode 40. FIG. 4B schematically shows redox cycling that occurs by oxidation and reduction of the test substance in the sample solution present between the first working electrode 20 and the second working electrode 40.

The sample solution 200 is injected from any of not-closed side surfaces of a space sandwiched between the first working electrode 20 and the second working electrode 40 with a syringe, a dropper and the like using a capillary phenomenon. The injected sample solution 200 is held by its surface tension so as to be in contact with the first working electrode 20, the second working electrode 40, the reference electrode 60, and the counter electrode 70.

As shown in FIG. 4B, for example, a reductant Red that is the test substance contained in the sample solution 200 is oxidized in the first working electrode 20 to become an oxidant Ox, and then reduced in the second working electrode 40 facing the first working electrode 20 to return to the original reductant Red. The reduced reductant Red repeats the oxidation reaction in the first working electrode 20 and the reduction reaction in the second working electrode 40, so that redox cycling occurs. During the oxidation reaction and the reduction reaction, an electric current flows through the first working electrode 20 and the second working electrode 40 respectively. This electric current value is measured by the dual potentiostat 91 and the potentiostat 92, whereby the test substance in the sample solution can be detected.

The separation distance between the first working electrode 20 and the second working electrode 40 is, for example, 20 nm or more and 3 μm or less. The separation distance may, however, be appropriately set as necessary in conformity with the condition of use. Describing it further, the shorter the separation distance, the shorter the migration distance of the test substance. As a result, the number of occurrences of redox cycling per unit time is increased, thus enabling a highly sensitive electrochemical measurement. Therefore, the shorter the separation distance, the better, in order to enhance the sensitivity of the electrochemical detector. However, the separation distance between the first working electrode 20 and the second working electrode 40 is required to exceed at least the size of the test substance. In particular, when the electrochemical detector 100 is used as a biosensor for measuring a protein and the like in a living body, since the size of the protein is about 20 nm, the separation distance between the first working electrode 20 and the second working electrode 40 is set to 20 nm or more. Also, when the living body is blood, blood components such as a red blood cell, a white blood cell and a platelet block a migration path of the protein in redox cycling, and become a factor for reducing the sensitivity of the electrochemical measurement. Therefore, from the viewpoint of preventing the blood components from going into the space sandwiched between the first working electrode 20 and the second working electrode 40, it is preferred that the separation distance is smaller than the size of the blood components. Among the red blood cell, the white blood cell, and the platelet, the smallest blood component is the platelet, and its size is about 3 μm. Therefore, the separation distance between the first working electrode 20 and the second working electrode 40 is set to 3 μm or less. Also, even in consideration of a working limit and working accuracy, the separation distance is 20 nm or more and 3 μm or less.

Next, with reference to FIG. 5A through FIG. 7B, an example of the method for producing the electrochemical detector 100 according to the first embodiment will be described.

Figure 5A:
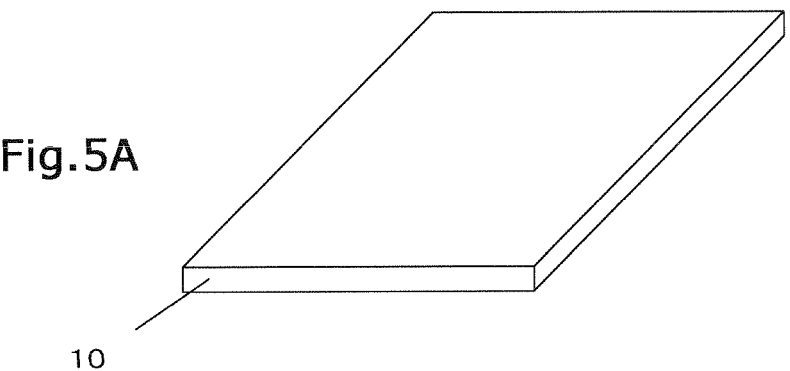
FIGS. 5A and 5B are perspective views for explaining steps of a method for producing the electrochemical detector 100 according to the first embodiment.

First, as shown in FIG. 5A, a first insulating substrate 10 is prepared. Although a glass substrate having a thickness of 1.5 mm was used, for example, in the first embodiment, other insulating substrates (for example, a resin substrate, a ceramic substrate, a quartz substrate, a silicon substrate with an oxide film) may also be used.

Figure 5B:
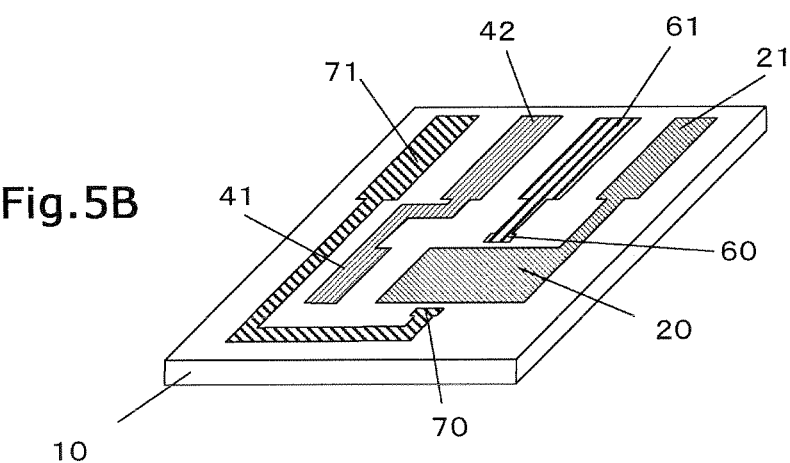

Next, as shown in FIG. 5B, one main surface of the insulating substrate 10 is metal-plated in a pattern to form an electrode pattern. This electrode pattern includes a first working electrode 20 and a lead-out electrode 21 connected thereto via wiring, a third electrode 41 and a lead-out electrode 42 connected thereto via wiring, a reference electrode 60 and a lead-out electrode 61 connected thereto via wiring, and a counter electrode 70 and a lead-out electrode 71 connected thereto via wiring.

In the first embodiment, although the metal plating is gold plating having a thickness of 3 μm, other metals (for example, platinum, silver, chromium, titanium, stainless) may also be used.

In the first embodiment, the insulating substrate 10 is metal-plated in a pattern to form the electrode pattern. However, other methods may also be used. For example, the entire surface of one main surface of the insulating substrate 10 is metal-plated, and etched in a pattern to form the electrode pattern. Also, a paste composition containing metal powder or conductive carbon powder may be printed in a pattern to form the electrode pattern. Further, a two-layer conductive layer may also be formed on the insulating substrate 10 to form the electrode pattern. For example, first, a first metal plating layer is formed on the entire surface of the one main surface of the insulating substrate 10. Then, the resultant surface is etched in a pattern to form a first layer. Further, on top of it, a second layer may be formed by performing metal plating or printing a paste composition containing metal powder or conductive carbon powder.

Figure 6A:
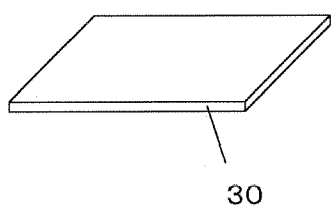
FIGS. 6A and 6B are perspective views for explaining steps of the method for producing the electrochemical detector 100 according to the first embodiment.

Next, as shown in FIG. 6A, a second insulating substrate 30 is prepared. Although a glass substrate having a thickness of 1 mm was used, for example, in the first embodiment, other insulating substrates (for example, a resin substrate, a ceramic substrate, a quartz substrate, a silicon substrate with an oxide film) may also be used.

Figure 6B:
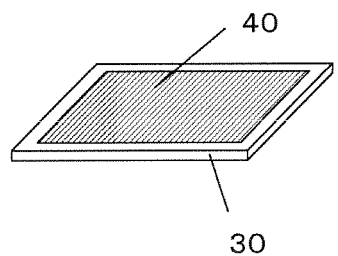

Next, as shown in FIG. 6B, one main surface of the insulating substrate 30 is metal-plated in a pattern to form a second working electrode 40.

In the first embodiment, although the metal plating is gold plating having a thickness of 3 μm, other metals (for example, platinum, silver, chromium, titanium, stainless) may also be used.

The formation of the second working electrode 40 on the insulating substrate 30 can also be performed by using a method similar to the above-described method for forming the electrode pattern on the insulating substrate 10.

Figure 7A:
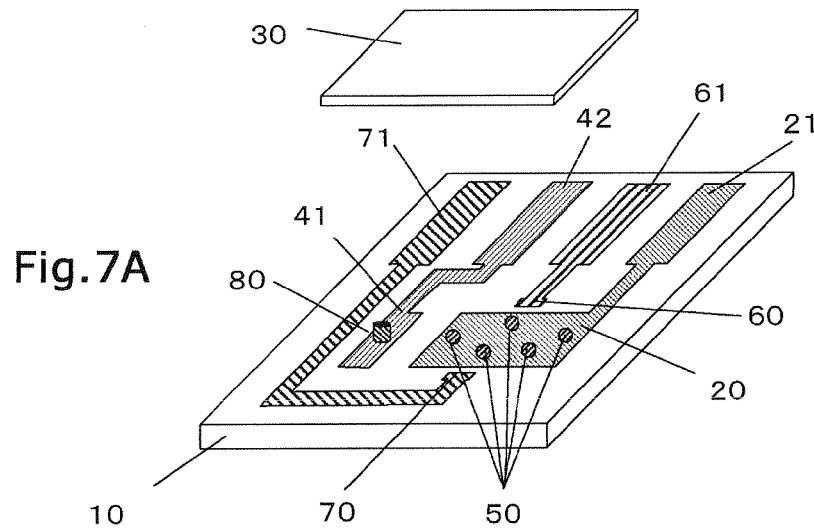
FIGS. 7A and 7B are perspective views for explaining steps of the method for producing the electrochemical detector 100 according to the first embodiment.

Next, as shown in FIG. 7A, a plurality of spacer particles 50 are placed on the first working electrode 20, and a connection member 80 is formed on a third electrode 41. Further, the second insulating substrate 30 is positioned with respect to the first insulating substrate and placed so that, in plan view, the first working electrode 20 and the second working electrode 40 overlap and face each other. As shown in FIG. 1B and FIG. 2C, the first working electrode 20 is smaller than the second working electrode 40. In the positioning, the second insulating substrate 30 is placed with respect to the first insulating substrate 10 so that, in plan view, the entire first working electrode 20 overlaps with the second working electrode 40.

In the first embodiment, although the insulating spacer particles 50 are spherical resin particles having a particle size of 1 μm, other particles (for example, silica, glass, ceramic) may also be used.

The plurality of spacer particles 50 can be placed on the first working electrode 20, for example, by spraying the spacer particles 50 so that they are adhered to the first working electrode 20. As methods for spraying the spacer particles 50, a wet-spray method, a dry-spray method and the like may be used. In the wet-spray method, the spacer particles 50 are adhered to the first working electrode 20 by spraying a liquid in which the spacer particles 50 are dispersed and evaporating a liquid. The wet-spray method has an advantage in that an adhesive material is contained in the liquid, whereby the spacer particles 50 can be adhered and fixed to the first working electrode 20. In the wet-spray method, in place of spraying the liquid in which the spacer particles 50 are dispersed, for example, this liquid may be applied onto the first working electrode 20. In the dry-spray method, charged spacer particles 50 are sprayed, so that the spacer particles 50 are adhered onto the first working electrode 20. The second insulating substrate 30 is fixed with respect to the first insulating substrate 10, and the plurality of spacer particles 50 are fixed by being sandwiched between the working electrodes 20 and 40. Therefore, also in the dry-spray method, positions of the plurality of spacer particles 50 are fixed. Here, the second insulating substrate 30 is fixed with respect to the first insulating substrate 10 by fixing the connection member 80 described below with respect to both the insulating substrates 10, 30.

In the first embodiment, although the connection member 80 is, for example, a paste composition containing silver powder, other materials (for example, a metal such as gold, aluminum, copper or solder, or a paste composition containing metal powder or conductive carbon powder) may also be used.

The connection member 80 can be formed, for example, by printing a paste composition. In this case, since the second working electrode 40 and the connection member 80 are joined in the next step, the connection member 80 remains uncured. When a metal such as gold, aluminum, or copper is used as the connection member 80, the connection member 80 can be formed also by a method in which a wire tip is fused by ultrasonic wave to form a metal bump.

Figure 7B:
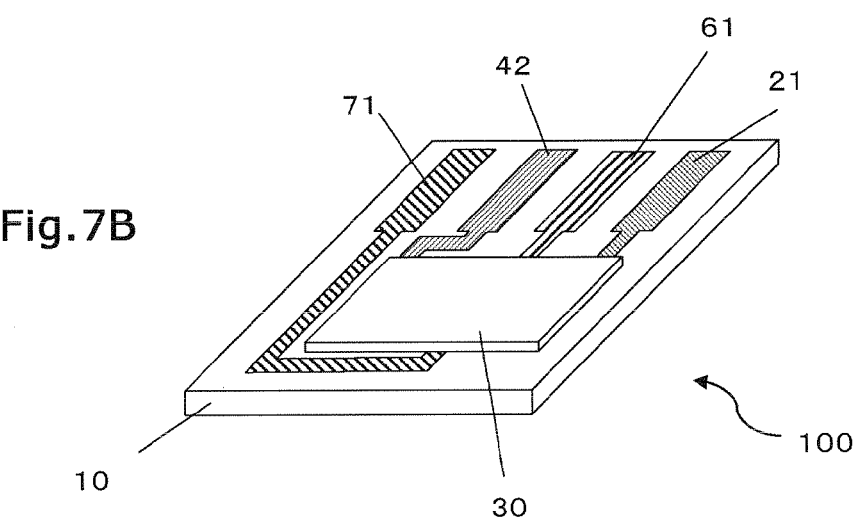

Next, as shown in FIG. 7B, the insulating substrate 30, in which the first working electrode and the second working electrode 40 are positioned so as to face each other, is overlapped with the insulating substrate 10 so as to sandwich therebetween the plurality of insulating spacers 50. Furthermore, the second working electrode 40 is connected to the connection member 80.

When the connection member 80 is a paste composition, it remains uncured in the previous step. In this case, connection of the second working electrode 40 and the connection member 80 can be performed by curing the paste composition by heat treatment. When the metal bump such as gold, aluminum or copper is used as the connection member 80, ultrasonic wave is applied to the insulating substrate 10 or 30 so that the second working electrode 40 and the tip of the metal bump are ultrasonic-welded, whereby the second working electrode 40 and the connection member 80 can be connected.

Second Embodiment

Figure 8:
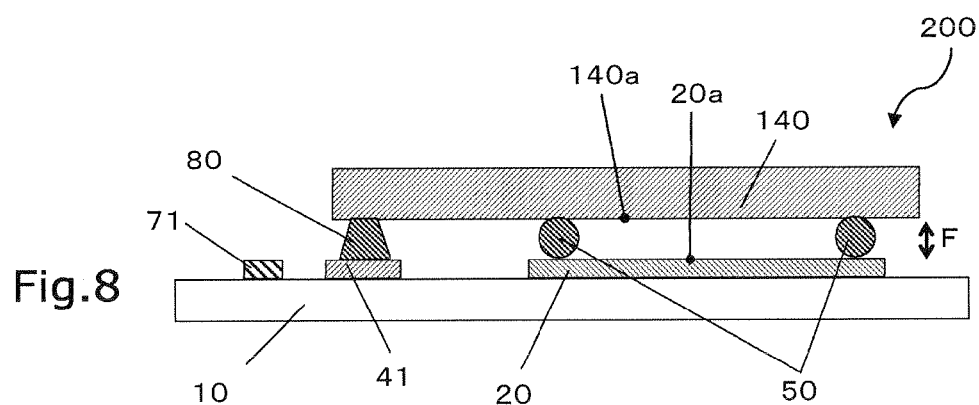
FIG. 8 is a view schematically showing the cross-sectional structure of an electrochemical detector used in a second embodiment.

With reference to FIG. 8, an electrochemical detector 200 of a second embodiment will be described. FIG. 8 is a view schematically showing the cross-sectional structure of the electrochemical detector used in the second embodiment. FIG. 8 corresponds to FIG. 1B.

The electrochemical detector 200 according to the second embodiment has a second working electrode 140 in place of the second working electrode 40 formed on the second insulating substrate 30. The second working electrode 140 is a metal plate having a second electrode surface 140a, and functions as a rigid body. Therefore, the second insulating substrate 30 is not used in the second embodiment.

Third Embodiment

Figure 9:
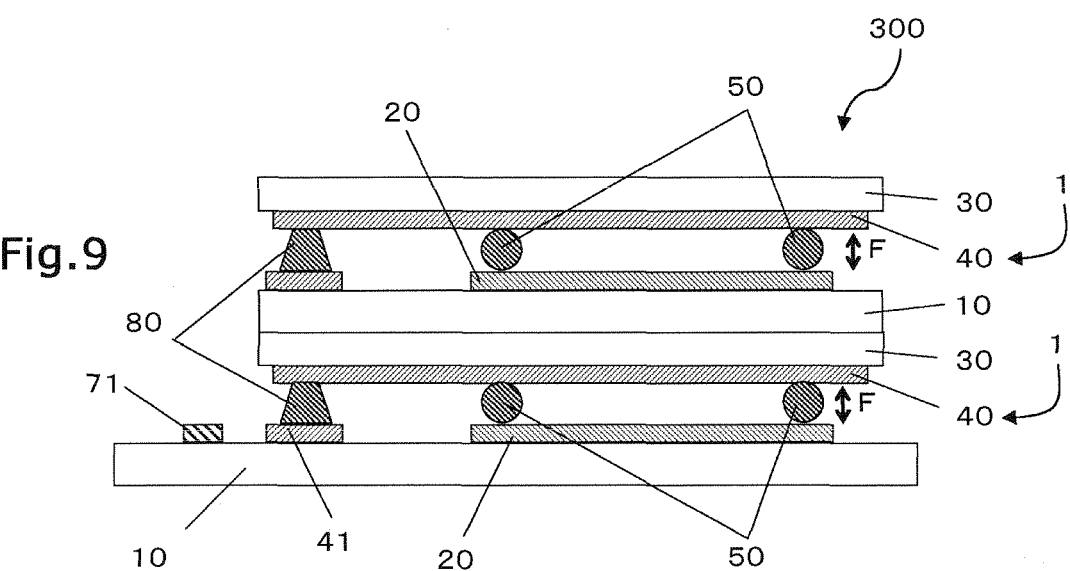
FIG. 9 is a view schematically showing the cross-sectional structure of an electrochemical detector used in a third embodiment.

With reference to FIG. 9, an electrochemical detector 300 of a third embodiment will be described. FIG. 9 is a view schematically showing the cross-sectional structure of the electrochemical detector used in the third embodiment. FIG. 9 corresponds to FIG. 1B.

The electrochemical detector 300 according to the third embodiment has two detection units 1. The two detection units 1 are placed along a direction parallel to electric field F. Each detection unit 1 has the first working electrode 20, the second working electrode 40, the plurality of spacers 50, the third electrode 41, and the connection member 80. The first working electrode 20, the second working electrode 40, and the plurality of spacers 50 are essential components of the detection unit 1. The third electrode 41 and the connection member 80 are selective elements of the detection unit 1. Further, the electrochemical detector 300 has the two first insulating substrates 10, and the two second insulating substrates 30 as a structure to support the two detection units 1. Similarly to the first embodiment, the first working electrode 20 and the second working electrode 40 are formed on the first insulating substrate 10 and on the second insulating substrate 30, respectively. On an upper surface of the second insulating substrate 30 of the lower detection unit 1, a lower surface of the first insulating substrate 10 of the upper detection unit 1 is fixed. Here, the two detection units 1 are superposed in the same posture.

Fourth Embodiment

Figure 10:
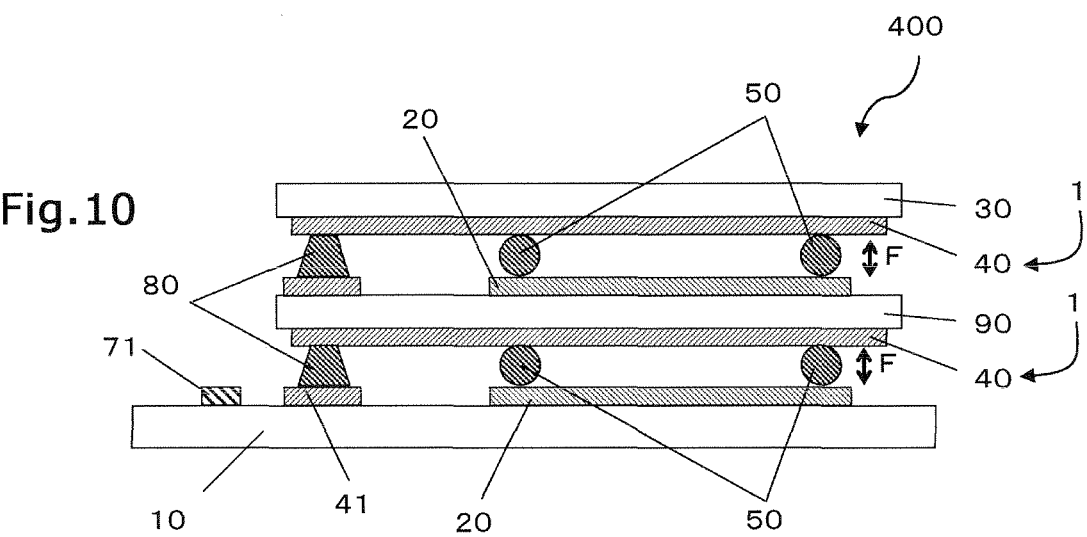
FIG. 10 is a view schematically showing the cross-sectional structure of an electrochemical detector used in a fourth embodiment.
Figure 11A:
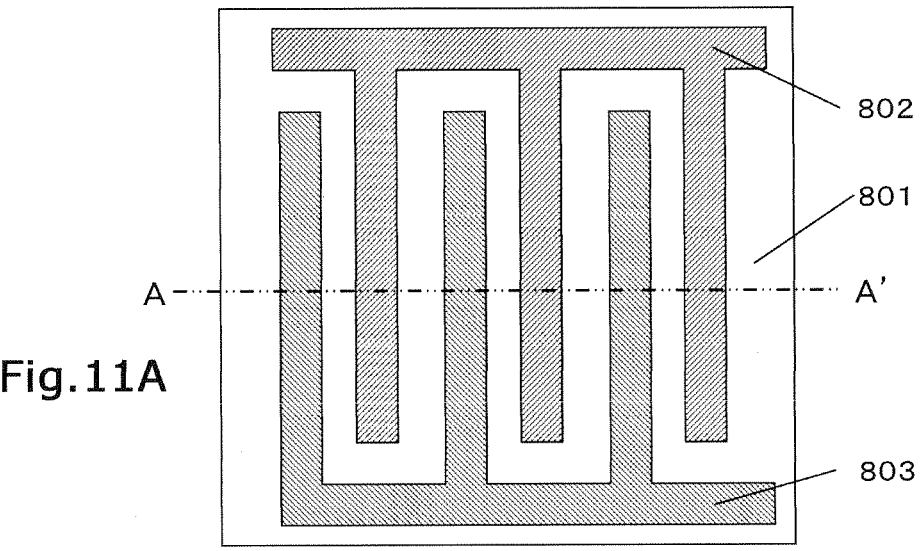
FIG. 11A is a plan view of a conventional electrochemical detector.
Figure 11B:
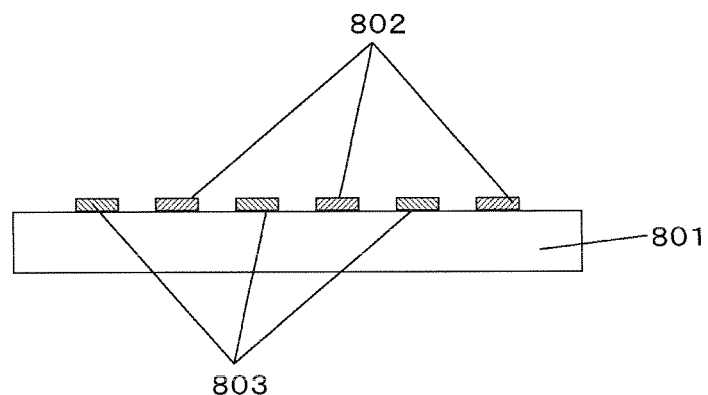
FIG. 11B is a cross-sectional view taken along line A-A of FIG. 11A.
Figure 12:
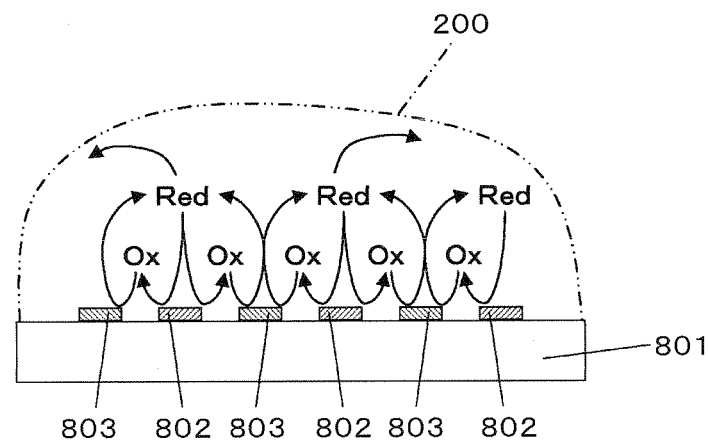
FIG. 12 a cross-sectional view for schematically describing redox cycling that occurs in the conventional electrochemical detector.

With reference to FIG. 10, an electrochemical detector 400 of a fourth embodiment will be described. FIG. 10 is a view schematically showing the cross-sectional structure of the electrochemical detector used in the fourth embodiment. FIG. 10 corresponds to FIG. 1B.

The electrochemical detector 400 according to the fourth embodiment also has two detection units 1. The electrochemical detector 400 according to the fourth embodiment is different from the electrochemical detector 300 according to the third embodiment, in the structure to support the detection units 1. The electrochemical detector 400 has the first insulating substrate 10, the second insulating substrate 30, and an insulating intermediate substrate 90 as the structure to support the two detection units 1. The first working electrode 20 and the third electrode 41 of the lower detection unit 1 are formed on the first insulating substrate 10. The second working electrode 40 of the upper detection unit 1 is formed on the second insulating substrate 30. The second working electrode 40 of the lower detection unit 1 is formed on a lower surface of the insulating intermediate substrate 90. The first working electrode 20 and the third electrode 41 of the upper detection unit 1 are formed on an upper surface of the intermediate substrate 90. That is, the intermediate substrate 90 according to the fourth embodiment is a substrate serving both as the intermediate first insulating substrate 10 and second insulating substrate 30 according to the third embodiment.

Effects of Embodiments

The electrochemical detectors 100-400 of the first to fourth embodiments and the method for producing the same have the following structure, whereby they have the following actions and effects:

(1) The electrochemical detectors according to the first to fourth embodiments detect a substance in a liquid by generating a redox cycle, wherein each of the electrochemical detectors 100-400 comprises: a first working electrode 20 having a first electrode surface 20a; a second working electrode 40 having a second electrode surface 40a; and a plurality of insulating spacers 50, wherein the first and second electrode surfaces 20a, 40a are placed so as to face each other so that an electric field F is formed between the first and second electrode surfaces 20a, 40a, and the plurality of spacers 50 are placed along the first and second electrode surfaces 20a, 40a so as to separate the first and second electrode surfaces 20a, 40a from each other.

Since the two working electrodes are formed on the same plane, unevenness in electric field occurs in the sample solution 200 held so as to be swollen from the plane. In this case, if the reductant Red and/or the oxidant Ox migrate to the region where the intensity of the electric field is low, the redox cycle is interrupted. On the other hand, in the first to fourth embodiments, since the two working electrodes 20, 40 are placed so as to face each other, the parallel electric field F is formed between the two working electrodes 20 and 40. Therefore, unevenness in the intensity of the electric field F hardly occurs in the sample solution 200 filled in the two working electrodes 20, 40. As a result, the redox cycle is hardly interrupted. That is, the detection sensitivity hardly deteriorates. Therefore, the electrochemical detectors 100-400 of the first to fourth embodiments enable a highly sensitive electrochemical measurement.

Further, in order to perform the highly sensitive measurement, it is preferred to reduce the distance between the two working electrodes 20 and 40. In the first to fourth embodiments, the separation distance between the two working electrodes 20 and 40 is determined by the spacers 50. Therefore, in the first to fourth embodiments, the separation distance between the two working electrodes 20 and 40 can be reduced without performing microfabrication of the electrodes. Therefore, the electrochemical detectors 100-400 of the first to fourth embodiments can be fabricated at a low cost, while enabling a highly sensitive electrochemical measurement.

(2) In the electrochemical detectors 100-400 according to the first to fourth embodiments, each of the spacers is particulate.

Therefore, in the electrochemical detectors 100-400 of the first to fourth embodiments, the separation distance between the two working electrodes 20 and 40 can be secured while suppressing a decrease in the volume of the sample solution 200 filled in the two working electrodes 20, 40.

(3) In the electrochemical detectors 100-400 according to the first to fourth embodiments, each of the spacers is formed of at least one shape selected from spherical and cylindrical.

Therefore, in the electrochemical detectors 100-400 of the first to fourth embodiments, the spacers can be formed relatively easily.

(4) In the electrochemical detectors 100-400 according to the first to fourth embodiments, the separation distance between the first working electrode surface 20a and the second working electrode surface 40a is 20 nm or more and 3 μm or less.

Therefore, the electrochemical detectors 100-400 of the first to fourth embodiments have high versatility to the size of the test substance.

(5) In the electrochemical detectors 100-400 according to the first to fourth embodiments, a surface density of the spacers on the first electrode surface 20a or the second electrode surface 40a is $0.01/mm^2$ or more and $1/mm^2$ or less.

Therefore, in the electrochemical detectors 100-400 of the first to fourth embodiments, the separation distance between the two working electrodes 20 and 40 can be secured while suppressing a decrease in the volume of the sample solution 200 filled in the two working electrodes 20, 40.

(6) Each of the electrochemical detectors 100-400 according to the first to fourth embodiment comprises at least one of a reference electrode 60 and a counter electrode 70.

Therefore, the electrochemical detectors 100-400 of the first to fourth embodiments can improve detection accuracy of the electrochemical measurement.

(7) In the electrochemical detectors 100-400 according to the first to fourth embodiments, each of the first and second working electrodes 20, 40 contains at least one kind of metal selected from gold and platinum.

Therefore, the electrochemical detectors 100-400 of the first to fourth embodiments can suppress degradation of the working electrodes 20, 40.

(8) In the electrochemical detectors 100-400 according to the first to fourth embodiments, each of the first and second working electrodes 20, 40 is formed of a paste composition containing conductive carbon powder.

Therefore, the electrochemical detectors 100-400 of the first to fourth embodiments can suppress degradation of the working electrodes 20, 40.

(9) Each of the electrochemical detectors 300, 400 according to the third and fourth embodiments comprises two detection units 1 which are placed along a direction parallel to the electric field. Each of the detection units 1 comprises the first working electrode 20, the second working electrode 40, and the plurality of spacers 50.

Therefore, in the electrochemical detectors 300, 400 of the third and fourth embodiments, a large amount of the sample solution can be placed, thus making it possible to improve detection accuracy of the electrochemical measurement.

(10) Each of the electrochemical detectors 100, 300, 400 according to the first, third and fourth embodiments comprises a first insulating substrate 10. The first working electrode 20 is formed on one main surface of a first insulating substrate 10.

Therefore, the electrochemical detectors 100, 300, 400 of the first, third and fourth embodiments can reduce the amount of the material required to produce the electrodes.

(11) Each of the electrochemical detectors 100-400 according to the first to fourth embodiments comprises a third electrode 41 formed on the one main surface of the first insulating substrate 10, and a connection member 80 for electrically connecting the second working electrode 40 and the third electrode 41.

Since wiring for applying a potential to the second working electrode 40 is formed on the first insulating substrate 10, it is possible to suppress an increase in the size of the second insulating substrate 40. The increase in the size of the second insulating substrate makes it difficult to fill the sample solution 200 between the working electrodes 20 and 40. Therefore, in the electrochemical detectors 100-400 of the first to fourth embodiments, the second insulating substrate 40 makes it possible to keep the placement of the sample solution 200 from being obstructed.

(12) In the electrochemical detectors 100-400 according to the first to fourth embodiments, the reference electrode 60 and/or the counter electrode 70 are formed on the one main surface of the first insulating substrate 10.

Since wiring for applying a potential to the reference electrode 60 and/or the counter electrode 70 are formed on the first insulating substrate 10, an increase in the size of the second insulating substrate 40 can be suppressed. Therefore, in the electrochemical detector 100 according to the present embodiment, the second insulating substrate 40 makes it possible to keep the placement of the sample solution 200 from being obstructed.

(13) Each of the electrochemical detectors 100-400 according to the first to fourth embodiments comprises a second insulating substrate 30. The second working electrode 40 is formed on one main surface of the second insulating substrate 30.

Therefore, the electrochemical detectors 100-400 of the first to fourth embodiments can reduce the amount of the material required to produce the electrodes.

(14) The electrochemical detector 400 according to the fourth embodiment comprises an insulating intermediate substrate 90 placed between the adjacent two detection units 1, and insulating end substrates (insulating substrates 10, 30). The first and second working electrodes 20, 40 are respectively formed on both main surfaces of the insulating intermediate substrate 90. The first or second working electrode 20, 40 is formed on one main surface of the insulating end substrate 10, 30.

Therefore, the electrochemical detector 400 according to the fourth embodiment can reduce the amount of the material required to produce the electrodes.

(15) The method for producing the electrochemical detectors 100-400 according to the first to fourth embodiments comprises: a step of placing a plurality of spacers 50 on a first working electrode 20 having a first electrode surface 20a; and a step of placing a second working electrode 40 having a second electrode surface 40a so as to face the first electrode surface 20a so that an electric field is formed between the first and second electrode surfaces 20a, 40a.

Therefore, the production method of the first to fourth embodiments can provide the electrochemical detector 100 which enables a highly sensitive electrochemical measurement and which can also be fabricated at a low cost.

(16) In the method for producing the electrochemical detectors 300, 400 according to the third and fourth embodiments, the step of placing the plurality of spacers 50 and the step of placing the second working electrode 40 are performed a plurality of times so that a plurality of detection units 1 are placed along a direction parallel to the electric field. Each of the detection units 1 has the first working electrode 20, the second working electrode 40, and the plurality of spacers 50.

Therefore, the production method of the third and fourth embodiments can provide the electrochemical detectors 300, 400 of the third and fourth embodiments in which a large amount of the sample solution can be placed, thus making it possible to improve detection accuracy of the electrochemical measurement.

(17) The method for producing the electrochemical detectors 300, 400 according to the third and fourth embodiments further comprises: a step of forming the first working electrode 20 on one main surface of a first insulating substrate 10; and a step of forming the second working electrode 40 on one main surface of a second insulating substrate 30.

Therefore, the production method of the third and fourth embodiments can reduce the amount of the material required to produce the electrodes.

(18) The method for producing the electrochemical detectors 100-400 according to the first to fourth embodiments comprises: a step of forming a third electrode 41 on the one main surface of the first insulating substrate 10; and a step of electrically connecting the second working electrode 40 and the third electrode 41 via a connection member 80.

Therefore, the production method of the first to fourth embodiments can provide the electrochemical detectors 100-400, in which the second insulating substrate 40 makes it possible to keep the placement of the sample solution 200 from being obstructed.

(19) The method for producing the electrochemical detectors 100-400 according to the first to fourth embodiments comprises: a step of forming at least one of a reference electrode 60 and a counter electrode 70 on the one main surface of the first insulating substrate 10.

Therefore, the production method of the first to fourth embodiments can provide the electrochemical detectors 100-400, in which the second insulating substrate 40 makes it possible to keep the placement of the sample solution 200 from being obstructed.

(20) The method for producing the electrochemical detector 400 according to the fourth embodiment further comprises: a step of forming the first or second working electrode 20, on each of both main surfaces of an insulating intermediate substrate 90 and placing the intermediate substrate 90 between the adjacent two detection units 1; and a step of forming the first or second working electrode 20, 40 on one main surface of an insulating end substrate 10, 30 and placing the end substrate 10, 30 on an open side of the detection unit.

Therefore, the electrochemical detector 400 according to the fourth embodiment can reduce the amount of the material required to produce the electrodes.

As described above, the present invention has been described by the preferred embodiments, but such description is not a limitation. It is a matter of course that various modifications can be made. For example, the first and second working electrodes having a rectangular shape were shown in the above embodiments, but it is not limited to this as long as the first working electrode 20 and the second working electrode 40 are placed so as to face each other. For example, they may also be circular or polygonal. Further, in FIG. 2C, the second working electrode is formed at a fixed distance away from an end of the second insulating substrate over its entire perimeter, but it is not limited thereto as long as it is placed so as to face the first working electrode 20. For example, it may be formed on the entire surface or at least part of the one main surface of the second insulating substrate. Further, in the electrochemical detector of FIG. 3, the method for connecting the electrochemical detector 100 to the dual potentiostat 91, the potentiostat 92, and the function generator 93 is not limited to this as long as the desired measurement is achieved. For example, the lead-out electrode 21, the lead-out electrode 42, the lead-out electrode 61, and the lead-out electrode 71 of the electrochemical detector 100 are all connected to the dual potentiostat 91, and different potentials are given respectively to the first working electrode 20 and the second working electrode 40 only by the dual potentiostat 91, using the potential of the reference electrode 60 as a reference potential.

INDUSTRIAL APPLICABILITY

The present invention can be applied, for example, to an electrochemical detector used for detectors, such as an electrochemical sensor and chromatography, in which the detectors are used for qualitative and quantitative analyses of ions, harmful substances, and physiologically active substances in a liquid.

REFERENCE SIGNS LIST 10 first insulating substrate
20 first working electrode
21 lead-out electrode
30 second insulating substrate
40 second working electrode
41 third electrode
42 lead-out electrode
50 insulating spacer particles
60 working electrode
61 lead-out electrode
70 counter electrode
71 lead-out electrode
80 connection member
91 dual potentiostat
92 potentiostat
93 function generator
200 sample solution
801 insulating substrate
802 working electrode
803 working electrode

The invention claimed is:

1. A method for producing an electrochemical detector, comprising:
a step of placing a plurality of spacers on a first working electrode having a first electrode surface; and
a step of placing a second working electrode having a second electrode surface so as to face the first electrode surface so that an electric field is formed between the first and second electrode surfaces, wherein
each of the spacers is particulate,
the step of placing the plurality of spacers and the step of placing the second working electrode are performed a plurality of times so that a plurality of detection units are placed along a direction parallel to the electric field, and
each of the detection units has the first working electrode, the second working electrode, and the plurality of spacers.

2. The method for producing an electrochemical detector according to claim 1, further comprising:
a step of forming the first working electrode on one main surface of the first insulating substrate; and
a step of forming the second working electrode on one main surface of the second insulating substrate.

3. The method for producing an electrochemical detector according to claim 2, comprising:
a step of forming a third electrode on the one main surface of the first insulating substrate; and
a step of electrically connecting the second working electrode and the third electrode via a connection member.

4. The method for producing an electrochemical detector according to claim 2, comprising:
a step of forming at least one of a reference electrode and a counter electrode on the one main surface of the first insulating substrate.

5. The method for producing an electrochemical detector according to claim 1, further comprising:
a step of forming the first or second working electrode on each of both main surfaces of an insulating intermediate substrate and placing the intermediate substrate between the adjacent two detection units; and
a step of forming the first or second working electrode on one main surface of an insulating end substrate and placing the end substrate on an open side of the detection unit.

6. An electrochemical detector for detecting a substance in a liquid by generating a redox cycle, the electrochemical detector comprising:
a first working electrode having a first electrode surface;
a second working electrode having a second electrode surface;
a plurality of insulating spacers;
a first insulating substrate, the first working electrode being formed on one main surface of the first insulating substrate;
a third electrode formed on the one main surface of the first insulating substrate; and
a connection member for electrically connecting the second working electrode and the third electrode, wherein
the first and second electrode surfaces are placed so as to face each other so that an electric field is formed between the first and second electrode surfaces,
the plurality of spacers are placed along the first and second electrode surfaces so as to separate the first and second electrode surfaces from each other,
each of the spacers is particulate,
the electrochemical detector comprises a plurality of detection units which are placed along a direction parallel to the electric field, and
each of the detection units comprises the first working electrode, the second working electrode, and the plurality of spacers.

7. The electrochemical detector according to claim 6, wherein each of the spacers is formed of at least one shape selected from spherical and cylindrical.

8. The electrochemical detector according to claim 6, wherein a separation distance between the first and second working electrode surfaces is 20 nm or more and 3 µm or less.

9. The electrochemical detector according to claim 6, wherein a surface density of the spacers on the first or second electrode surface is $0.01/mm^2$ or more and $1/mm^2$ or less.

10. The electrochemical detector according to claim 6, comprising at least one of a reference electrode and a counter electrode.

11. The electrochemical detector according to claim 6, wherein
each of the first and second working electrodes contains at least one kind of metal selected from gold and platinum.

12. The electrochemical detector according to claim 6, wherein
each of the first and second working electrodes is formed of a paste composition containing conductive carbon powder.

13. An electrochemical detector for detecting a substance in a liquid by generating a redox cycle, the electrochemical detector comprising:
a first working electrode having a first electrode surface;
a second working electrode having a second electrode surface;
a plurality of insulating spacers;
an insulating intermediate substrate placed between the adjacent two detection units; and an insulating end substrate being placed on an open side of the detection unit, wherein the first and second electrode surfaces are placed so as to face each other so that an electric field is formed between the first and second electrode surfaces, the plurality of spacers are placed along the first and second electrode surfaces so as to separate the first and second electrode surfaces from each other, each of the spacers is particulate, the electrochemical detector comprises a plurality of detection units which are placed along a direction parallel to the electric field, each of the detection units comprises the first working electrode, the second working electrode, and the plurality of spacers, the first or second working electrode is formed on each of both main surfaces of the insulating intermediate substrate, and the first or second working electrode is formed on one main surface of the insulating end substrate.

14. The electrochemical detector according to claim 13, wherein each of the spacers is formed of at least one shape selected from spherical and cylindrical.

15. The electrochemical detector according to claim 13, wherein a separation distance between the first and second working electrode surfaces is 20 nm or more and 3 μm or less.

16. The electrochemical detector according to claim 13, wherein a surface density of the spacers on the first or second electrode surface is $0.01/mm^2$ or more and $1/mm^2$ or less.

17. The electrochemical detector according to claim 13, comprising at least one of a reference electrode and a counter electrode.

18. The electrochemical detector according to claim 13, wherein each of the first and second working electrodes contains at least one kind of metal selected from gold and platinum.

19. The electrochemical detector according to claim 13, wherein each of the first and second working electrodes is formed of a paste composition containing conductive carbon powder.

20. The electrochemical detector according to claim 13, comprising a first insulating substrate, wherein the first working electrode is formed on one main surface of the first insulating substrate.

\* \* \* \* \*